US009594048B2

(12) United States Patent
Oya et al.

(10) Patent No.: US 9,594,048 B2
(45) Date of Patent: Mar. 14, 2017

(54) HEATER AND GAS SENSOR ELEMENT

(71) Applicant: NGK Spark Plug Co., Ltd., Nagoya-shi, Aichi (JP)

(72) Inventors: Seiji Oya, Fuso-cho (JP); Yuta Oishi, Fuso-cho (JP)

(73) Assignee: NGK SPARK PLUG CO., LTD., Nagoya-shi (JP)

( * ) Notice: Subject to any disclaimer, the term of this patent is extended or adjusted under 35 U.S.C. 154(b) by 239 days.

(21) Appl. No.: 14/289,685

(22) Filed: May 29, 2014

(65) Prior Publication Data
US 2015/0001077 A1 Jan. 1, 2015

(30) Foreign Application Priority Data

Jun. 27, 2013 (JP) .................................. 2013-134560

(51) Int. Cl.
*G01N 27/00* (2006.01)
*G01N 27/406* (2006.01)
*H05B 3/26* (2006.01)

(52) U.S. Cl.
CPC ......... *G01N 27/4067* (2013.01); *H05B 3/265* (2013.01)

(58) Field of Classification Search
CPC ...... G01N 27/00; G01N 27/4067; H05B 3/16; H05B 3/265
USPC .............. 422/83, 98; 204/424; 219/548, 553
See application file for complete search history.

(56) References Cited

U.S. PATENT DOCUMENTS

| 4,634,514 | A | * | 1/1987 | Nishizawa et al. ........... 204/406 |
| 4,797,194 | A | * | 1/1989 | Mase et al. .................... 204/425 |
| 4,883,947 | A | * | 11/1989 | Murase et al. ................ 219/553 |
| 4,952,903 | A | * | 8/1990 | Shibata et al. .................. 338/34 |
| 5,895,591 | A | * | 4/1999 | Kojima et al. ................ 219/209 |
| 2003/0006139 | A1 | * | 1/2003 | Noda et al. .................... 204/424 |
| 2003/0136676 | A1 | * | 7/2003 | Miwa et al. .................. 204/426 |

(Continued)

FOREIGN PATENT DOCUMENTS

| EP | 0 963 137 A2 | 6/1999 | ............... H05B 3/26 |
| EP | 0 963 137 B1 | 12/1999 | ............... H05B 3/26 |

(Continued)

OTHER PUBLICATIONS

Office Action issued in corresponding Japanese Patent Application No. 2013-134560 dated Nov. 8, 2016.

*Primary Examiner* — Brian J Sines
(74) *Attorney, Agent, or Firm* — Kusner & Jaffe

(57) ABSTRACT

A heater which realizes both reduction of power consumption and improvement of durability against thermal shock. The heater includes a ceramic substrate formed of a ceramic material containing alumina as a main component; and a heat-generating resistor provided on the ceramic substrate and having a heat-generating portion and a lead portion, the heat-generating resistor containing, as a main component, one or more metals selected from the group consisting of platinum (Pt), palladium (Pd), and rhodium (Rh), or an alloy of any of these, and a ceramic material which is the same as the ceramic material of the ceramic substrate. In the heater, the ratio of the resistance of the heat-generating portion to the sum of the resistances of the heat-generating portion and the lead portion is 76 to 95%, and the heat-generating portion has a thickness of 1 to 6 μm.

8 Claims, 3 Drawing Sheets

(56) References Cited

U.S. PATENT DOCUMENTS

| | | | |
|---|---|---|---|
| 2004/0069630 A1 | 4/2004 | Tanaka et al. | 204/424 |
| 2012/0103808 A1* | 5/2012 | Igarashi et al. | 204/424 |
| 2013/0048627 A1* | 2/2013 | Satou | 219/552 |

FOREIGN PATENT DOCUMENTS

| | | | |
|---|---|---|---|
| JP | H08-21813 A | 1/1996 | G01N 27/12 |
| JP | 2000-58237 | 2/2000 | H05B 3/20 |
| JP | 2003-279531 A | 10/2003 | G01N 27/04 |
| JP | 2003-315303 A | 11/2003 | G01N 27/409 |
| JP | 2004-151017 A | 5/2004 | G01N 27/419 |
| JP | 2004-178942 A | 6/2004 | H05B 3/03 |
| JP | 2013-96888 | 5/2013 | G01N 24/409 |

* cited by examiner

HEATER AND GAS SENSOR ELEMENT

FIELD OF THE INVENTION

The present invention relates to a heater, and to a gas sensor element.

BACKGROUND OF THE INVENTION

Reduction of power consumption is required for a heater including a ceramic substrate formed mainly of alumina, and a heat-generating resistor provided on the ceramic substrate. In order to reduce the power consumption of the heater, desirably, generation of heat is suppressed to a minimum possible level in a lead portion of the heat-generating resistor, the resistor including the lead portion and a heat-generating portion. Therefore, desirably, the ratio of the resistance of the heat-generating portion to the sum of the resistances of the heat-generating portion and the lead portion (hereinafter the ratio may be referred to as "heating-portion resistance ratio") is increased. For example, Japanese Patent Application Laid-Open (kokai) No. 2000-58237 ("Patent Document 1") discloses a heater including a heat-generating resistor formed of tungsten, wherein the heating-portion resistance ratio is 75% or more.

In general, when the heating-portion resistance ratio of the heat-generating resistor increases, a heat-generating portion of the resistor has increased temperature elevation rate, whereby a ceramic substrate provided on the resistor is rapidly heated. However, regarding the heater described in Patent Document 1, no particular attention is paid to durability against peeling of the heat-generating resistor from the ceramic substrate, which could be caused by repeated rapid heating and cooling, since the difference in thermal expansion coefficient between tungsten and alumina is relatively small. In contrast, in the case of a heater including a heat-generating resistor containing a noble metal (e.g., platinum, palladium, or rhodium) as a main component, and a ceramic substrate containing alumina as a main component, the difference in thermal expansion coefficient between the noble metal and alumina is large. Thus, when heating-portion resistance ratio increases, the heat-generating resistor is more likely to be peeled from the ceramic substrate due to thermal shock. Therefore, demand has arisen for a technique regarding a heater which realizes both reduction of power consumption and improvement of durability against thermal shock, the heater including a ceramic substrate containing alumina as a main component, and a heat-generating resistor containing a noble metal as a main component.

SUMMARY OF THE INVENTION

The present invention has been accomplished for solving the aforementioned problems, and the invention provides the following modes.

(1) In one mode of the present invention, there is provided a heater comprising a ceramic substrate formed of a ceramic material containing alumina as a main component; and a heat-generating resistor provided on the ceramic substrate and having a heat-generating portion and a lead portion, the heat-generating resistor containing, as a main component, one or more metals selected from the group consisting of platinum (Pt), palladium (Pd), and rhodium (Rh), or an alloy of any of these, and a ceramic material which is the same as the ceramic material of the ceramic substrate, wherein the ratio of the resistance of the heat-generating portion to the sum of the resistances of the heat-generating portion and the lead portion is 76 to 95%, and the heat-generating portion has a thickness of 1 to 6 µm. In this heater, since the thickness of the heat-generating portion is relatively small (i.e., 1 to 6 µm), even when the heating-portion resistance ratio is adjusted to a relatively high level (i.e., 76 to 95%) for reduction of power consumption, generation of large stress, which would otherwise be caused by the difference in thermal expansion coefficient between the ceramic substrate and the heat-generating resistor, can be suppressed. Therefore, the heater realizes both reduction of power consumption and improvement of durability against thermal shock.

(2) In the aforementioned heater, the heat-generating portion may have a thickness of 1 to 4 µm. In this case, since the thickness of the heat-generating portion is further reduced, generation of large stress, which would otherwise be caused by the difference in thermal expansion coefficient between the ceramic substrate and the heat-generating resistor, can be suppressed. Therefore, the heater exhibits further improved durability against thermal shock.

(3) In the aforementioned heater, the heat-generating portion may have a ceramic content of 10 to 35 vol. %. In this case, while adhesion between the heat-generating portion and the ceramic substrate is improved, occurrence of wire breakage or the like, which would otherwise be caused by sublimation of a main component (e.g., platinum) from the heat-generating portion, can be suppressed. Therefore, the heater exhibits improved durability.

(4) In the aforementioned heater, the thickness of the heat-generating portion may be 50% or less that of the lead portion. Also in this case, since the thickness of the heat-generating portion can be reduced, generation of stress, which would otherwise be caused by the difference in thermal expansion coefficient between the ceramic substrate and the heat-generating resistor, can be suppressed. Therefore, the heater exhibits improved durability against thermal shock.

(5) In another mode of the present invention, there is provided a gas sensor element comprising a sensor cell for detecting a particular gas component contained in a gas to be measured, the sensor cell including a solid electrolyte layer, and a pair of electrodes formed on the solid electrolyte layer; and the aforementioned heater for heating the sensor cell, the heater being stacked directly or via another member on the sensor cell. This gas sensor element also realizes reduction of power consumption and improvement of durability against thermal shock.

The present invention may be implemented in various forms other than the aforementioned heater or gas sensor element; for example, an internal combustion engine or vehicle including the gas sensor element.

DETAILED DESCRIPTION OF THE INVENTION

A. Configuration of Gas Sensor

Figure 1:
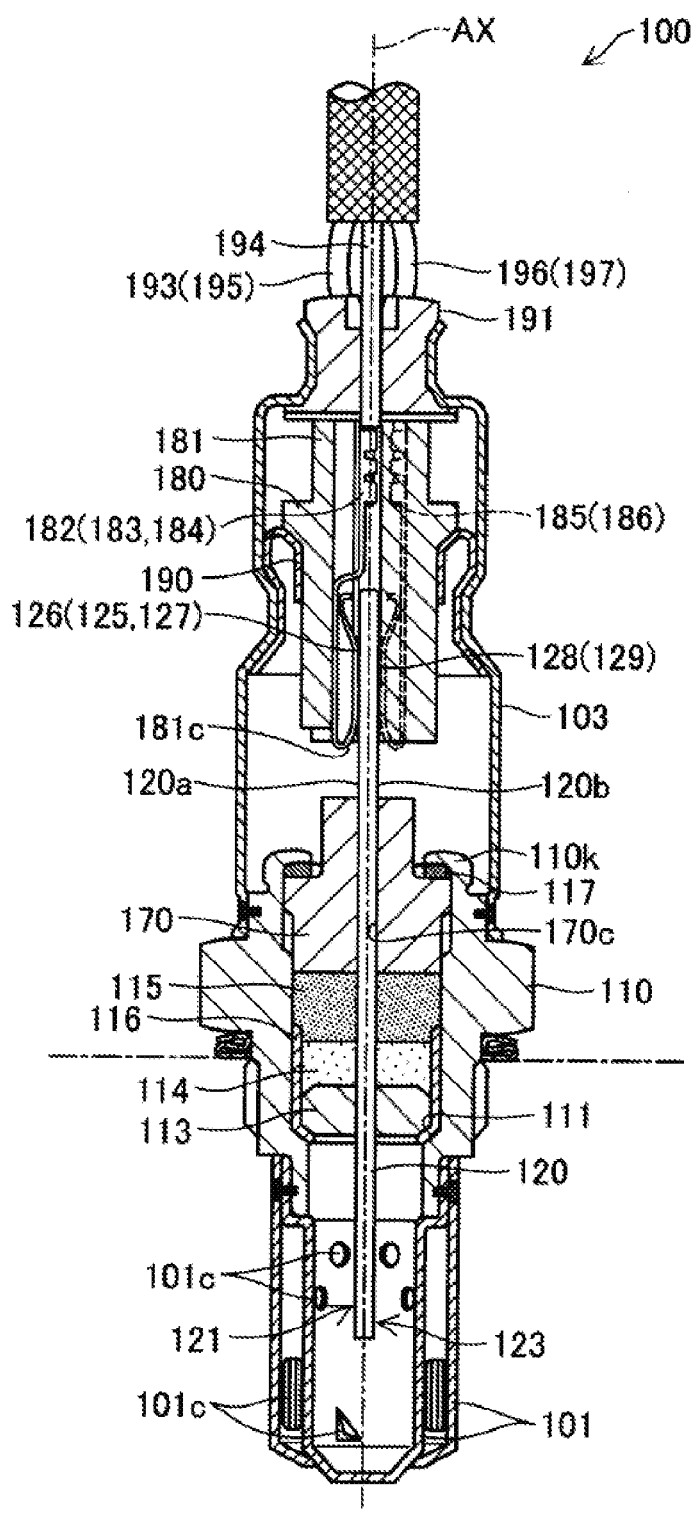
FIG. 1 is a cross-sectional view of a gas sensor.

FIG. 1 is a cross-sectional view of a gas sensor 100. In FIG. 1, the lower side corresponds to the forward end side in the direction of an axis AX, and the upper side corresponds to the rear end side in the direction of the axis AX. This gas sensor 100 corresponds to a wide-range air-fuel ratio sensor for determining the oxygen concentration of exhaust gas discharged from an internal combustion engine.

As shown in FIG. 1, the gas sensor 100 includes a metallic shell 110, a gas sensor element 120, a metallic tubular sheath 103, and a connection structure 180.

The metallic shell 110 has a tubular shape and extends in the direction of the axis AX. The metallic shell 110 includes therein a shelf portion 111 projecting inwardly in a radial direction. The metallic shell 110 includes therein a tubular ceramic holder 113 formed of alumina; a first powder filler layer 114 formed of talc powder; a second powder filler layer 115 formed of talc powder; and a tubular ceramic sleeve 170 formed of alumina, which are sequentially provided from the forward end side toward the rear end side. The metallic shell 110 also includes therein a tubular metallic cup 116 which is integrated with the gas sensor element 120 together with the ceramic holder 113 and the first powder filler layer 114. Also, a crimp ring 117 is provided between the ceramic sleeve 170 and a rear end portion 110k of the metallic shell 110.

The ceramic holder 113 is provided in the metallic cup 116, and a forward end portion of the ceramic holder 113 is engaged with the shelf portion 111 of the metallic shell 110 with the intervention of the metallic cup 116. The gas sensor element 120 is inserted in the ceramic holder 113. The entirety of the first powder filler layer 114 and a forward end portion of the second powder filler layer 115 are provided in the metallic cup 116. The air tightness between the metallic shell 110 and the gas sensor element 120 is secured by means of the second powder filler layer 115.

The plate-like gas sensor element 120 extends in the direction of the axis AX, and is provided in the interior of the metallic shell 110. A forward end portion of the gas sensor element 120 projects from the metallic shell 110 toward the forward end of the gas sensor, and a rear end portion of the gas sensor element 120 projects from the metallic shell 110 toward the rear end of the gas sensor. The gas sensor element 120 includes a sensor cell 130 (see FIG. 2) capable of determining the oxygen concentration of exhaust gas, and a heater 160 (see FIG. 2) capable of heating the sensor cell 130. The configuration of the gas sensor element 120 will be described in detail hereinbelow.

The tubular ceramic sleeve 170 extends along the axis AX, and has an axial hole 170c of rectangular cross section. The ceramic sleeve 170 supports the plate-like gas sensor element 120 which is inserted in the rectangular axial hole 170c. The rear end portion 110k of the metallic shell 110 is bent inwardly in a radial direction, and is crimped to the rear end surface of the ceramic sleeve 170 via the crimp ring 117, whereby the ceramic sleeve 170 is fixed in the metallic shell 110.

On the forward end side of the metallic shell 110, a bottomed tubular protector 101 having a dual structure is fixed through laser welding so as to cover a forward end portion of the gas sensor element 120 projecting from the metallic shell 110. A plurality of introduction holes 101c are provided at specific positions on the protector 101 so that exhaust gas can be introduced therein.

The metallic tubular sheath 103 is fixed through laser welding on the rear end side of the metallic shell 110. The metallic tubular sheath 103 includes therein a connection structure 180. The connection structure 180 is formed of a ceramic separator 181, three sensor connection terminals 182, 183, and 184, and two heater connection terminals 185 and 186. The separator 181 accommodates the sensor connection terminals 182, 183, and 184, and the heater connection terminals 185 and 186 such that the terminals are not in contact with one another; i.e., the terminals are isolated from one another.

The connection structure 180 is attached on the rear end side of the gas sensor element 120 so as to be spaced from the ceramic sleeve 170. A rear end portion of the gas sensor element 120 projecting from the rear end of the ceramic sleeve 170 is inserted in an opening 181c of the separator 181. The sensor connection terminals 182, 183, and 184 are in elastic contact with and electrically connected to sensor electrode pads 125, 126, and 127 (see FIG. 2) of the gas sensor element 120, respectively. Meanwhile, the heater connection terminals 185 and 186 are in elastic contact with and electrically connected to heater electrode pads 128 and 129 (see FIG. 2) of the gas sensor element 120, respectively. The connection structure 180 is held in the metallic tubular sheath 103 such that the connection structure 180 is biased against the below-described grommet 191 by means of a generally tubular biasing bracket 190 provided around the connection structure 180.

The metallic tubular sheath 103 includes, in a rear end portion thereof, a fluororubber-made grommet 191 in which three sensor lead wires 193, 194, and 195 and two heater lead wires 196 and 197 are inserted. The sensor lead wires 193, 194, and 195 are inserted in and electrically connected to the connection structure 180 such that forward end portions of the lead wires 193, 194, and 195 are crimped by means of the sensor connection terminals 182, 183, and 184. Also, the heater lead wires 196 and 197 are inserted in and electrically connected to the connection structure 180 such that forward end portions of the lead wires 196 and 197 are crimped by means of the heater connection terminals 185 and 186. The sensor lead wire 193 is connected to the Ip electrode pad 125 (see FIG. 2) of the gas sensor element 120 via the sensor connection terminal 182, and the sensor lead wire 194 is connected to the COM electrode pad 126 (see FIG. 2) of the gas sensor element 120 via the sensor connection terminal 183. The sensor lead wire 195 is connected to the Vs electrode pad 127 (see FIG. 2) of the gas sensor element 120 via the sensor connection terminal 184.

B. Configuration of Gas Sensor Element

Figure 2:
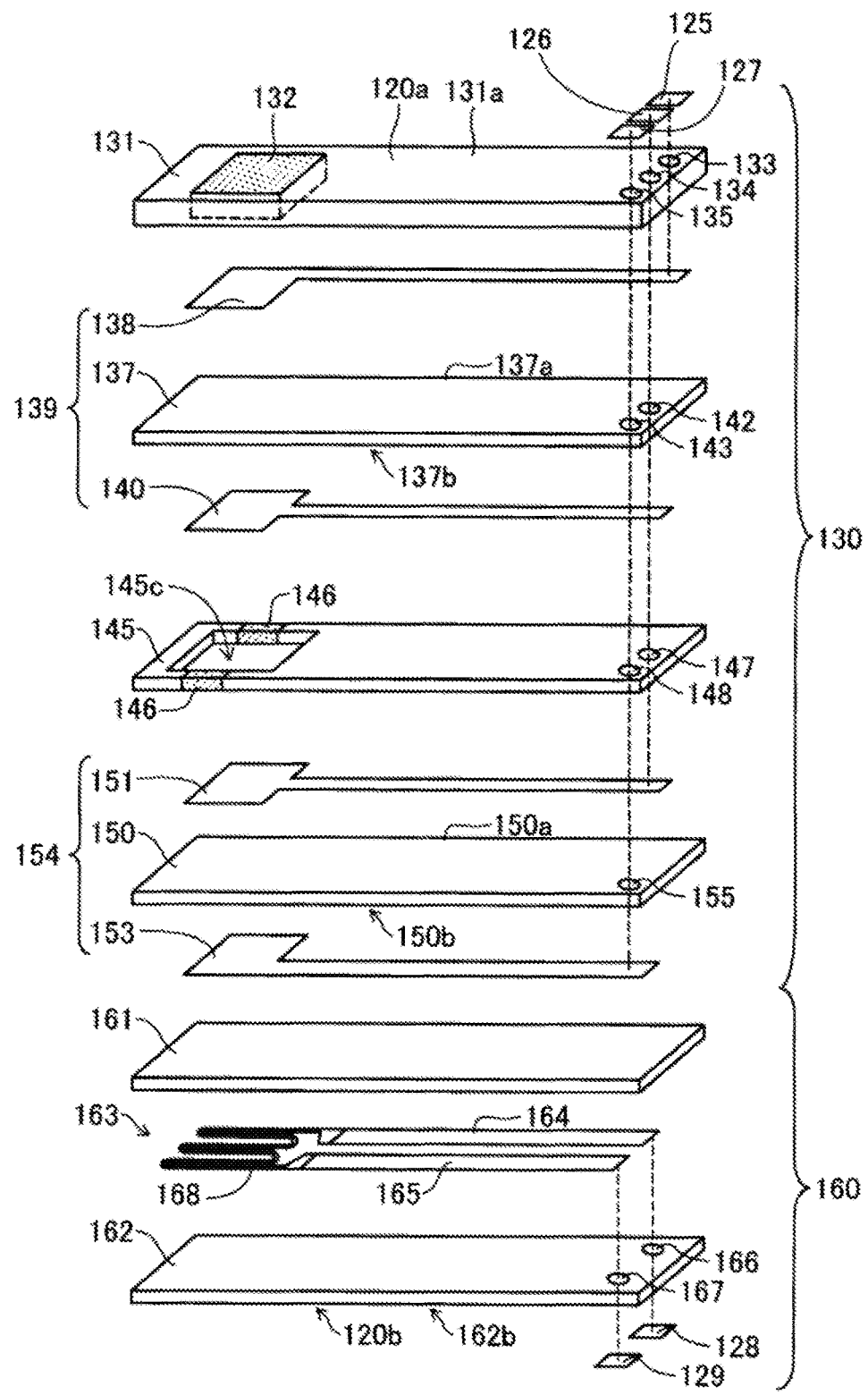
FIG. 2 is an exploded perspective view of a gas sensor element.

FIG. 2 is an exploded perspective view of the gas sensor element 120. The gas sensor element 120 includes a plate-like sensor cell 130 extending in the axial direction (horizontal direction in FIG. 2), and a plate-like heater 160 extending in the axial direction, the sensor cell 130 and the heater 160 being stacked with each other. The sensor cell 130 and the heater 160 are integrated through firing. In FIG. 2, the left side corresponds to the forward end side shown in FIG. 1, and the right side corresponds to the rear end side shown in FIG. 1.

The sensor cell 130 includes a protective layer 131, a pump cell 139, a spacer 145, and an electromotive cell 154, each of which assumes a plate-like shape, and which are sequentially stacked from a first plate surface 120a toward a second plate surface 120b.

The protective layer 131 is mainly formed of alumina. A porous body 132 is embedded in a forward end portion of the protective layer 131. The protective layer 131 has a first surface 131a, which serves as the first plate surface 120a of the gas sensor element 120. In the vicinity of the rear end of the first surface 131a, the aforementioned three sensor electrode pads (i.e., the Ip electrode pad 125, the COM electrode pad 126, and the Vs electrode pad 127) are arranged at specific intervals in a direction orthogonal to the axial direction. As shown by broken lines in FIG. 2, the Ip electrode pad 125, the COM electrode pad 126, and the Vs electrode pad 127 are electrically connected to three via conductors 133, 134, and 135, respectively, the via conductors being formed in the vicinity of the rear end of the protective layer 131 so as to penetrate therethrough.

The pump cell 139 generally includes a solid electrolyte layer 137 mainly formed of zirconia, a first electrode 138, and a second electrode 140, which electrodes will be described hereinbelow. Two via conductors 142 and 143 are formed in the vicinity of the rear end of the solid electrolyte layer 137 so as to penetrate therethrough. The via conductors 142 and 143 are respectively electrically connected to the via conductors 134 and 135 penetrating the protective layer 131.

The solid electrolyte layer 137 has, on a first surface 137*a* thereof (on the upper side of FIG. 2), a rectangular, porous first electrode 138 mainly formed of platinum (Pt). The first electrode 138 is electrically connected to the via conductor 133 penetrating the protective layer 131. Therefore, the first electrode 138 is electrically conducted to the Ip electrode pad 125 with the intervention of the via conductor 133. The first electrode 138 is exposed to exhaust gas through the porous body 132 embedded in the protective layer 131.

The solid electrolyte layer 137 has, on a second surface 137*b* thereof (on the lower side of FIG. 2), a rectangular, porous second electrode 140 mainly formed of Pt. The second electrode 140 is electrically connected to the via conductor 142 penetrating the solid electrolyte layer 137. Therefore, the second electrode 140 is electrically conducted to the COM electrode pad 126 with the intervention of the via conductors 142 and 134.

The spacer 145 is mainly formed of alumina, and has a rectangular opening at a forward end portion thereof. Since the spacer 145 is sandwiched between the pump cell 139 and the electromotive cell 154, this opening forms a gas detection chamber 145*c*. Each of opposite side walls of the gas detection chamber 145*c* is partially provided with a porous body 146 for securing ventilation between the inside of the detection chamber 145*c* and the outside thereof. The porous body 146 is formed of porous alumina. Two via conductors 147 and 148 are formed in the vicinity of the rear end of the spacer 145 so as to penetrate therethrough. The via conductor 147 is electrically connected to the second electrode 140, whereas the via conductor 148 is electrically connected to the via conductor 143 penetrating the solid electrolyte layer 137.

The electromotive cell 154 generally includes a solid electrolyte layer 150 mainly formed of zirconia, a third electrode 151, and a fourth electrode 153, which electrodes will be described hereinbelow. A via conductor 155 is formed in the vicinity of the rear end of the solid electrolyte layer 150 so as to penetrate therethrough. The via conductor 155 is electrically connected to the via conductor 148 penetrating the spacer 145.

The solid electrolyte layer 150 has, on a first surface 150*a* thereof (on the upper side of FIG. 2), a rectangular, porous third electrode 151 mainly formed of Pt. The third electrode 151 is electrically connected to the via conductor 147 penetrating the spacer 145. Therefore, the third electrode 151 is electrically conducted to the COM electrode pad 126 with the intervention of the via conductor 147, the second electrode 140, the via conductor 142, and the via conductor 134. That is, the third electrode 151 and the second electrode 140, each of which is connected to the COM electrode pad 126, have the same electric potential.

The solid electrolyte layer 150 has, on a second surface 150*b* thereof (on the lower side of FIG. 2), a rectangular, porous fourth electrode 153 mainly formed of Pt. The fourth electrode 153 is electrically connected to the via conductor 155 penetrating the solid electrolyte layer 150. Therefore, the fourth electrode 153 is electrically conducted to the Vs electrode pad 127 with the intervention of the via conductors 155, 148, 143, and 135.

The heater 160 includes a first ceramic substrate 161 and a second ceramic substrate 162, each of which assumes a plate-like shape and contains alumina as a main component. The first ceramic substrate 161 is disposed on the side toward the first plate surface 120*a*, and the second ceramic substrate 162 is disposed on the side toward the second plate surface 120*b*. A heat-generating resistor 163 is provided between the first ceramic substrate 161 and the second ceramic substrate 162.

Figure 3:
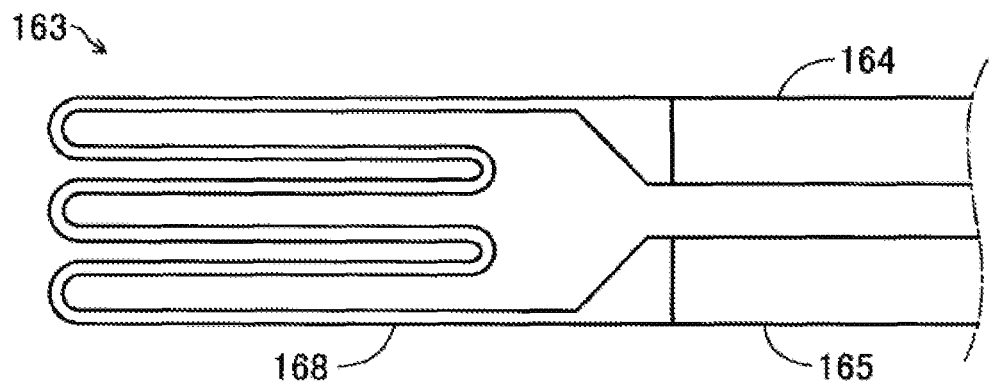
FIG. 3 is an explanatory view of the configuration of a heat-generating resistor.

FIG. 3 illustrates the configuration of the heat-generating resistor. The heat-generating resistor 163 contains a noble metal as a main component, and also contains the same ceramic component as forming the first ceramic substrate 161 or the second ceramic substrate 162. The noble metal employed in the heat-generating resistor 163 may be one or more metals selected from the group consisting of platinum (Pt), palladium (Pd), and rhodium (Rh), or an alloy of any of these (e.g., Pt—Pd alloy, Pt—Rh alloy, or Pt—Pd—Rh alloy). The heat-generating resistor 163 includes a heat-generating portion 168, and lead portions 164 and 165. In the heat-generating resistor 163, the heat-generating portion 168 has a meandering shape. The heat-generating portion 168 is located on the forward end side in the axial direction. The lead portions 164 and 165 are electrically connected to two ends of the heat-generating portion 168, and extend straight toward the rear end side.

Two via conductors 166 and 167 are formed in the vicinity of the rear end of the second ceramic substrate 162 (see FIG. 2) so as to penetrate therethrough. The second ceramic substrate 162 has a second surface 162b, which serves as the second plate surface 120*b* of the gas sensor element 120. In the vicinity of the rear end of the second surface 162b, the aforementioned two heater electrode pads 128 and 129 are arranged in a direction orthogonal to the axial direction. The heater electrode pad 128 is electrically connected to the lead portion 164 with the intervention of the via conductor 166, whereas the heater electrode pad 129 is electrically connected to the lead portion 165 with the intervention of the via conductor 167. The heat-generating portion 168 generates heat through application of voltage from the heater electrode pad 128 or 129 via the lead portion 164 or 165.

In the present embodiment, the heating-portion resistance ratio; i.e., the ratio of the resistance R1 of the heat-generating portion 168 to the sum R3 of the resistance R1 of the heat-generating portion 168 and the resistance R2 of the lead portions 164 and 165 (R3=R1+R2), is 76 to 95%. The thickness of the heat-generating portion 168 is 1 to 6 μm, preferably 1 to 4 μm. The ceramic content of the heat-generating portion 168 is preferably 10 to 35 vol. %. The thickness of the heat-generating portion 168 is preferably 50% or less that of the lead portion 164 or 165. The reason why the heating-portion resistance ratio, the thickness of the heat-generating portion 168, and the ceramic content of the heat-generating portion 168 are determined to be the aforementioned values will be described below on the basis of the results of the following performance evaluation tests.

The heat-generating portion 168 may be formed through, for example, the method described in Japanese Patent Application Laid-Open (kokai) No. 2013-96888. In this method, firstly, a printing paste is prepared. The printing paste contains a noble metal, ceramic particles, a binder, and a solvent. The binder employed may be, for example, a binder of high polymerization degree having a viscosity of 150 Pa·S or more, such as ethylcellulose (e.g., Ethocel (registered trademark), product of Nisshin & Co., Ltd.), polyvinyl butyral (e.g., trade name: BH-S, product of Sekisui Chemical Co., Ltd.), cellulose acetate, alkyd resin, phenolic resin, acrylic resin, epoxy resin, or polyurethane. The solvent employed may be a single solvent selected from among butyl carbitol, butyl carbitol acetate, terpineol, terpineol acetate, dihydroterpineol, and ethyl carbitol acetate, or a mixture of any of these solvents. The solid content of the paste (i.e., the amount of the noble metal and the ceramic particles contained in the paste) can be adjusted to 30 to 70 wt. % by employing such a binder and such a solvent. After preparation of such a printing paste, the paste is applied, through printing, to an object of interest (i.e., the first ceramic substrate 161 or the second ceramic substrate 162) via a metal mask having an opening corresponding to the meandering shape of the heat-generating portion 168. When the aforementioned binder of high polymerization degree is employed, the solvent content of the printing paste can be increased. Therefore, the printing paste can be thinly applied to the object of interest. When the thus-applied paste is dried, and firing is carried out at a specific temperature, the heat-generating portion 168 is formed in a thin film state. The heat-generating portion 168 may be formed through, instead of the aforementioned method, for example, high-mesh screen printing, pad printing, plating, or ink jetting.

Operation of the gas sensor 100 having the aforementioned configuration will now be described for reference. Upon use of the gas sensor 100, firstly, the heater 160 is heated to a specific temperature (e.g., 700 to 800° C.), to thereby activate the sensor cell 130. Subsequently, a minute current Icp (about 15 µA) is caused to flow through the electromotive cell 154 via the Vs electrode pad 127 so that the fourth electrode 153 functions as an oxygen reference electrode. In this state, when the theoretical air-fuel ratio is maintained in an atmosphere in the gas detection chamber 145c, a voltage of 450 mV is generated between the electromotive cell 154 and the oxygen reference electrode in which the oxygen concentration is maintained almost constant. By means of a known electrical circuit, the current Ip flowing through the pump cell 137 is appropriately adjusted so that the voltage Vs of the electromotive cell 154 is controlled to be 450 mV, to thereby maintain the theoretical air-fuel ratio in an atmosphere in the gas detection chamber 145c. When the gas sensor 100 is operated in this manner, the oxygen concentration of exhaust gas can be determined on the basis of the current Ip required for maintaining the theoretical air-fuel ratio in the gas detection chamber 145c.

In the above-described the gas sensor 100 according to the present embodiment, since the thickness of the heat-generating portion is relatively small (i.e., 1 to 6 µm, preferably 1 to 4 µm), even when the heating-portion resistance ratio is adjusted to a relatively high level (i.e., 76 to 95%) for reduction of power consumption (i.e., for suppression of heat generation at the lead portion 164 or 165), generation of stress, which would otherwise be caused by the difference in thermal expansion coefficient between the ceramic substrate and the heat-generating resistor, can be suppressed. Therefore, the power consumption of the gas sensor 100 (heater 160) can be reduced. Furthermore, the durability of the heater 160 against thermal shock (i.e., the thermal shock resistance of the heater 160) can be improved. In the present embodiment, the thickness of the heat-generating portion 168 is reduced; specifically, the thickness of the heat-generating portion 168 is adjusted to be 50% or less that of the lead portion 164 or 165. Therefore, since generation of stress, which would otherwise be caused by the difference in thermal expansion coefficient between the ceramic substrate and the heat-generating resistor, can be suppressed, the thermal shock resistance of the heater 160 can be improved.

In the gas sensor 100 according to the present embodiment, the ceramic content of the heat-generating portion 168 is adjusted to 10 to 35 vol. %. Therefore, while adhesion between the heat-generating portion 168 and the ceramic substrate 161 or 162 is improved, deterioration of the durability of the gas sensor 100, which would otherwise be caused by sublimation of the noble metal from the heat-generating portion 168, can be suppressed.

C. Performance Evaluation Test

Table 1 shows the results of performance evaluation tests carried out on the gas sensor 100. In the evaluation tests, samples of the gas sensor 100 were prepared by varying the heating-portion resistance ratio, the ceramic content of the heat-generating portion 168, and the thickness of the heat-generating portion 168 (10 samples for each sample No.), and each sample was evaluated in terms of thermal shock resistance, power consumption, and durability. As shown in Table 1 (test results), the ceramic content of the heat-generating portion of each sample was maintained at 20 vol. %, and the heating-portion resistance ratio and the thickness of the heat-generating portion 168 were varied. The heating-portion resistance ratio can be calculated on the basis of the resistances of the heat-generating portion 168 and the lead portions 164 and 165 as measured through a hole provided in the second ceramic substrate 162 of the gas sensor element 120 by means of, for example, a tool manufactured by Minitor Co., Ltd. The thickness of the heat-generating portion 168 can be determined by observing a polished cross section of the heat-generating portion 168 under a scanning electron microscope (SEM). The ceramic content of the heat-generating portion 168 can be determined through image analysis of a polished cross section of the heat-generating portion 168 by means of an SEM.

TABLE 1

| Sample No. | Heating-portion resistance ratio (%) | Thickness of heat-generating portion (µm) | Ceramic content (vol. %) | Thermal shock resistance | Power consumption | Durability |
|---|---|---|---|---|---|---|
| 1 | 65 | 8 | 20 | AA | — | BB |
| 2 | 73 | 8 | 20 | AA | CC | BB |
| 3 | 76 | 8 | 20 | CC | BB | BB |
| 4 | 80 | 0.7 | 20 | AA | BB | DD |
| 5 | 80 | 1 | 20 | AA | BB | BB |
| 6 | 80 | 4 | 20 | AA | BB | BB |
| 7 | 80 | 6 | 20 | BB | BB | BB |
| 8 | 80 | 8 | 20 | CC | BB | BB |
| 9 | 95 | 8 | 20 | CC | BB | BB |
| 10 | 97 | 8 | 20 | DD | BB | DD |

For evaluation of thermal shock resistance, each sample of the gas sensor 100 was subjected to 10,000 cycles of thermal treatment (each cycle including application of a voltage 1.5 times the rated voltage (e.g., 21 V), and heating of the heater 160 to 1,000° C., followed by cooling), and it was determined whether or not removal or cracking occurred in the heat-generating portion 168 and the ceramic substrates 161 and 162 during these cycles. In Table 1, "DD" corresponds to the case where removal or cracking occurred in one or more samples within cycles; "CC" corresponds to the case where neither removal nor cracking occurred in all the 10 samples after cycles, but removal or cracking occurred in one or more samples within 1,000 cycles; "BB" corresponds to the case where neither removal nor cracking occurred in all the 10 samples after 1,000 cycles, but removal or cracking occurred in one or more samples within 10,000 cycles; and "AA" corresponds to the case where neither removal nor cracking occurred in all the 10 samples after 10,000 cycles.

For evaluation of power consumption, the power consumption of each sample was determined on the basis of the power consumption of sample No. 1 of the gas sensor 100 when being commonly controlled so as to attain a temperature of 800° C. In Table 1, "CC" corresponds to the case where all the 10 samples exhibited a percent improvement in power consumption of less than 30% with respect to sample No. 1 of the gas sensor 100; and "BB" corresponds to the case where all the 10 samples exhibited a percent improvement in power consumption of 30% or more with respect to sample No. 1 of the gas sensor 100.

For evaluation of durability, it was determined whether or not wire breakage occurred in each sample within 500 hours after application of a voltage to the heater 160 for achieving the rated temperature (e.g., 800° C.) of the gas sensor 100. In Table 1, "DD" corresponds to the case where wire breakage occurred in at least one of 10 samples within 500 hours; and "BB" corresponds to the case where no wire breakage occurred in all the 10 samples within 500 hours.

As is clear from the evaluation results of samples Nos. 1 to 3 and 8 to 10 shown in Table 1, when the heating-portion resistance ratio is 76% or more, power consumption is improved, whereas when the thickness of the heat-generating portion 168 is large (8 μm), thermal shock resistance is impaired as the heating-portion resistance ratio increases. Particularly, sample No. 10 (heating-portion resistance ratio: as high as 97%) was evaluated as exhibiting the worst thermal shock resistance and durability. Conceivably, this is attributed to the fact that removal or cracking occurs at the forward end of the heat-generating portion 168 due to concentration of heat generation.

In the case where the heating-portion resistance ratio was 80%, when the thickness of the heat-generating portion 168 was 0.7 μm (sample No. 4), durability was evaluated as poor. Conceivably, this is attributed to the fact that since the heat-generating portion 168 is excessively thin, the noble metal contained in the heat-generating portion 168 is sublimated, whereby wire breakage occurs. Meanwhile, when the thickness of the heat-generating portion 168 was 8 μm (sample No. 8), thermal shock resistance was evaluated as poor. Conceivably, this is attributed to the fact that since the heat-generating portion 168 is excessively thick, large stress is generated in the heat-generating portion 168, whereby removal or cracking occurs between the heat-generating portion 168 and the ceramic substrate 161 or 162.

As is clear from the evaluation results in terms of thermal shock resistance, power consumption, and durability shown above in Table 1, the heating-portion resistance ratio is preferably 76 to 95%, and the thickness of the heat-generating portion 168 is preferably 1 to 6 μm, more preferably 1 to 4 μm.

Table 2 shows the evaluation results of samples prepared by varying the ceramic content of the heat-generating portion 168 while the heating-portion resistance ratio and the thickness of the heat-generating portion 168 were maintained at preferred values shown in Table 1 (heating-portion resistance ratio: 80%, thickness: 4 μm).

TABLE 2

| Sample No. | Heating-portion resistance ratio (%) | Thickness of heat-generating portion (μm) | Ceramic content (vol. %) | Thermal shock resistance | Power consumption | Durability |
|---|---|---|---|---|---|---|
| 11 | 80 | 4 | 8 | CC | BB | BB |
| 12 | 80 | 4 | 10 | AA | BB | BB |
| 13 | 80 | 4 | 35 | AA | BB | BB |

As is clear from the evaluation results shown in Table 2, sample No. 11 with a low ceramic content of the heat-generating portion 168 exhibits poor thermal shock resistance. Conceivably, this is attributed to insufficient adhesion between the heat-generating portion 168 and the ceramic substrate 161 or 162. Although not shown in Table 2, when the ceramic content of the heat-generating portion 168 is excessively high (i.e., more than 35 vol. %), linkage between noble metal particles is impaired in the heat-generating portion 168, resulting in insufficient electrical conductivity, and thus poor heat-generating performance.

As is clear from the evaluation results in terms of thermal shock resistance, power consumption, and durability shown above in Table 2, the ceramic content of the heat-generating portion 168 is preferably 10 to 35 vol. %.

D. Other Embodiments

Application of the heater 160 according to the aforementioned embodiment is not limited to the gas sensor 100 (i.e., a wide-range air-fuel ratio sensor), and the heater 160 may be applied to a variety of other sensors, including a zirconia oxygen sensor and an $NO_x$ sensor.

The present invention is not limited to the above-described embodiments, and various modifications may be made without departing from the scope of the present invention. For example, the technical characteristics described in the embodiments corresponding to those of the modes described in the section "Summary of the Invention" may be appropriately replaced or combined in order to partially or completely solve the aforementioned problems, or to partially or completely achieve the aforementioned effects. Unless the technical characteristics are described as essential ones in the present specification, they may be appropriately omitted.

DESCRIPTION OF REFERENCE NUMERALS

100: gas sensor
101: protector
101c: introduction hole
103: metallic tubular sheath
110: metallic shell
110k: rear end portion
111: shelf portion
113: ceramic holder
114: first powder filler layer
115: second powder filler layer
116: metallic cup
117: crimp ring
120: gas sensor element 120a: first plate surface
120b: second plate surface
121: gas detection portion
123: heater portion
125: Ip electrode pad
126: COM electrode pad
127: Vs electrode pad
128, 129: heater electrode
130: sensor cell
131: protective layer
132: porous body
133, 134, 135: via conductor
137: solid electrolyte layer
138: first electrode
139: pump cell
140: second electrode
142, 143, 147, 148, 155, 166, 167: via conductor
145: spacer
145c: gas detection chamber
146: porous body
150: solid electrolyte layer
151: third electrode
153: fourth electrode
154: electromotive cell
160: heater
161: first ceramic substrate
162: second ceramic substrate
163: heat-generating resistor
164, 165: lead portion
168: heat-generating portion
170: ceramic sleeve
170c: axial hole
180: connection structure
181: separator
181c: opening
182, 183, 184: sensor connection terminal
185, 186: heater connection terminal
190: biasing bracket
191: grommet
193, 194, 195: sensor lead wire
196, 197: heater lead wire
AX: axis Having described the invention, the following is claimed:

1. A heater comprising:
a ceramic substrate formed of a ceramic material containing alumina as a main component; and
a heat-generating resistor provided on the ceramic substrate and having a heat-generating portion and a lead portion, the heat-generating resistor containing, as a main component, one or more metals selected from the group consisting of platinum (Pt), palladium (Pd), and rhodium (Rh), or an alloy of any of these, and a ceramic material which is the same as the ceramic material of the ceramic substrate, wherein
the ratio of the resistance of the heat-generating portion to the sum of the resistances of the heat-generating portion and the lead portion is 76 to 95%; and
the heat-generating portion has a thickness of 1 to 6 μm.

2. A heater according to claim 1, wherein the heat-generating portion has a thickness of 1 to 4 μm.

3. A heater according to claim 1, wherein the heat-generating portion has a ceramic content of 10 to 35 vol. %.

4. A heater according to claim 1, wherein the thickness of the heat-generating portion is 50% or less that of the lead portion.

5. A gas sensor element comprising:
a sensor cell for detecting a particular gas component contained in a gas to be measured, the sensor cell including a solid electrolyte layer, and a pair of electrodes formed on the solid electrolyte layer; and
a heater for heating the sensor cell, the heater comprising:
a ceramic substrate formed of a ceramic material containing alumina as a main component, and
a heat-generating resistor provided on the ceramic substrate and having a heat-generating portion and a lead portion, the heat-generating resistor containing, as a main component, one or more metals selected from the group consisting of platinum (Pt), palladium (Pd), and rhodium (Rh), or an alloy of any of these, and a ceramic material which is the same as the ceramic material of the ceramic substrate, wherein
the ratio of the resistance of the heat-generating portion to the sum of the resistances of the heat-generating portion and the lead portion is 76 to 95%, and
the heat-generating portion has a thickness of 1 to 6 μm; and
wherein the heater is stacked directly or via another member on the sensor cell.

6. A gas sensor element according to claim 5, wherein the heat-generating portion has a thickness of 1 to 4 μm.

7. A gas sensor element according to claim 5, wherein the heat-generating portion has a ceramic content of 10 to 35 vol. %.

8. A gas sensor element according to claim 5, wherein the thickness of the heat-generating portion is 50% or less that of the lead portion.

* * * * *